US012410242B2

(12) United States Patent
Gong et al.

(10) Patent No.: US 12,410,242 B2
(45) Date of Patent: Sep. 9, 2025

(54) C-BASED SINGLE DOMAIN ANTIBODY FOR NEUTRALIZING RESPIRATORY SYNCYTIAL VIRUS AND APPLICATION THEREOF

(71) Applicant: WUHAN BANKE BIOTECHNOLOGY CO., LTD., Wuhan (CN)

(72) Inventors: Rui Gong, Wuhan (CN); Haiwei Zhang, Wuhan (CN); Ye Qin, Wuhan (CN)

(73) Assignee: WUHAN BANKE BIOTECHNOLOGY CO., LTD., Wuhan (CN)

(*) Notice: Subject to any disclaimer, the term of this patent is extended or adjusted under 35 U.S.C. 154(b) by 0 days.

(21) Appl. No.: 18/777,836

(22) Filed: Jul. 19, 2024

(65) Prior Publication Data
US 2025/0042977 A1 Feb. 6, 2025

Related U.S. Application Data

(63) Continuation of application No. PCT/CN2023/115623, filed on Aug. 29, 2023.

(30) Foreign Application Priority Data

Aug. 30, 2022 (CN) ......................... 202211049964.6

(51) Int. Cl.
*C07K 16/10* (2006.01)
*A61K 39/00* (2006.01)
*A61P 31/14* (2006.01)

(52) U.S. Cl.
CPC .......... *C07K 16/1027* (2013.01); *A61P 31/14* (2018.01); *A61K 2039/505* (2013.01); *C07K 2317/524* (2013.01); *C07K 2317/569* (2013.01); *C07K 2317/76* (2013.01)

(58) Field of Classification Search
CPC .......... C07K 16/1027; C07K 2317/524; C07K 2317/569; C07K 2317/76; A61P 31/14; A61K 2039/505
See application file for complete search history.

(56) References Cited

U.S. PATENT DOCUMENTS

| | | | | |
|---|---|---|---|---|
| 5,762,905 | A * | 6/1998 | Burton | A61K 51/1006 424/9.4 |
| 2013/0189247 | A1* | 7/2013 | Bramhill | C07K 16/2812 530/387.3 |
| 2018/0264103 | A1 | 9/2018 | Zhao et al. | |

FOREIGN PATENT DOCUMENTS

| | | | | |
|---|---|---|---|---|
| CA | 3044682 | A1 * | 6/2018 | A61K 35/17 |
| CN | 108101992 | A | 6/2018 | |
| CN | 108129566 | A | 6/2018 | |
| CN | 108472343 | A | 8/2018 | |
| CN | 108676094 | A | 10/2018 | |
| CN | 114805561 | A | 7/2022 | |
| CN | 116063468 | A | 5/2023 | |
| CN | 117050166 | A * | 11/2023 | |
| EP | 3124042 | A1 | 2/2017 | |
| KR | 20200136774 | A | 12/2020 | |
| WO | 2018099968 | A1 | 6/2018 | |

OTHER PUBLICATIONS

Gong et al. 2023. CN 117050166 A. Machine Translation. (Year: 2023).*
International Search Report issued in corresponding International application No. PCT/CN2023/115623, mailed Nov. 16, 2023.
Written Opinion of the International Search Authority in corresponding International application No. PCT/CN2023/115623, mailed Nov. 16, 2023.
Application and the research progress of nanobodies, Renren Jiang et al., vol. 33, Issue 3, 2013, pp. 307-315.
"Chain A, Ig gamma-1 chain C region", National Center for Biotechnology Information, https://www.ncbi.nlm.nih.gov/protein/3DJ9A?report=genbank&log$=prtalign&blastrank=1&RID=3YD1FDWA016.

* cited by examiner

*Primary Examiner* — Janet L Andres
*Assistant Examiner* — Carey Alexander Stuart
(74) *Attorney, Agent, or Firm* — HOWARD M COHN and Associates, LLC

(57) ABSTRACT

The present disclosure relates to a C-based single domain antibody that neutralizes respiratory syncytial virus (RSV) and its application thereof. The C-based single domain antibody of the present disclosure is a neutralizing antibody against RSV F protein, can inhibit the viral entry into host cells, and can be used for the prevention, treatment and diagnosis of RSV, as well as for further studying the mechanism of RSV infection. The C-based single domain antibody has a smaller molecular weight, better tissue permeability and the ability to bind to antigenic epitope with steric hindrance effect; it can be expressed in multiple expression systems, including prokaryotic, yeast, and mammalian cells. The C-based single domain antibody has a low production cost and a short production cycle; it has a wide range of administration routes and can be administered through nasal drops, nasal spray, spray, aerosol inhalation, intramuscular injection, intravenous injection, subcutaneous injection, etc.

8 Claims, 4 Drawing Sheets

Specification includes a Sequence Listing.

A

B

```
                        SEQUENCE LISTING

Sequence total quantity: 42
SEQ ID NO: 1            moltype = AA   length = 10
FEATURE                 Location/Qualifiers
source                  1..10
                        mol_type = protein
                        organism = synthetic construct
SEQUENCE: 1
GYNPYDFPII                                                              10

SEQ ID NO: 2            moltype = AA   length = 10
FEATURE                 Location/Qualifiers
source                  1..10
                        mol_type = protein
                        organism = synthetic construct
SEQUENCE: 2
GYNPYDFPIV                                                              10

SEQ ID NO: 3            moltype = AA   length = 9
FEATURE                 Location/Qualifiers
source                  1..9
                        mol_type = protein
```

```
                        -continued
                        organism = synthetic construct
SEQUENCE: 3
DENSYNTDS                                                                 9

SEQ ID NO: 4            moltype = AA   length = 9
FEATURE                 Location/Qualifiers
source                  1..9
                        mol_type = protein
                        organism = synthetic construct
SEQUENCE: 4
DENSYNTDR                                                                 9

SEQ ID NO: 5            moltype = AA   length = 9
FEATURE                 Location/Qualifiers
source                  1..9
                        mol_type = protein
                        organism = synthetic construct
SEQUENCE: 5
EENSYNTDR                                                                 9

SEQ ID NO: 6            moltype = AA   length = 16
FEATURE                 Location/Qualifiers
source                  1..16
                        mol_type = protein
                        organism = synthetic construct
SEQUENCE: 6
AREGGSSGEW YYDLWG                                                        16

SEQ ID NO: 7            moltype = AA   length = 16
FEATURE                 Location/Qualifiers
source                  1..16
                        mol_type = protein
                        organism = synthetic construct
SEQUENCE: 7
ARVGGSSGEW YYDLWG                                                        16

SEQ ID NO: 8            moltype = AA   length = 16
FEATURE                 Location/Qualifiers
source                  1..16
                        mol_type = protein
                        organism = synthetic construct
SEQUENCE: 8
AREGGSSGEW YYNLWG                                                        16

SEQ ID NO: 9            moltype = AA   length = 16
FEATURE                 Location/Qualifiers
source                  1..16
                        mol_type = protein
                        organism = synthetic construct
SEQUENCE: 9
AREGGSSGDW YYDLWG                                                        16

SEQ ID NO: 10           moltype = AA   length = 114
FEATURE                 Location/Qualifiers
source                  1..114
                        mol_type = protein
                        organism = synthetic construct
SEQUENCE: 10
PSVLCLPPKP KDTLVISRTP EVTCVVSGYN PYDFPIIKFK WYVDGVEVDN AKVKPRDENS         60
YNTDSVVSKL TVLHQDWLNG KEYKCKVSAR EGGSSGEWYY DLWGPIECTI SKAK              114

SEQ ID NO: 11           moltype = AA   length = 114
FEATURE                 Location/Qualifiers
source                  1..114
                        mol_type = protein
                        organism = synthetic construct
SEQUENCE: 11
PSVSCLPPKP KDTFVISRTP EVTCVVSGYN PYDFPIIKFK WYVDGVEVDN AKVKPRDENS         60
YNTDSVVSKL TVLHQDWLNG KEYKCKVSAR EGGSSGEWYY DLWGPIECTI SKAK              114

SEQ ID NO: 12           moltype = AA   length = 114
FEATURE                 Location/Qualifiers
source                  1..114
                        mol_type = protein
                        organism = synthetic construct
SEQUENCE: 12
PSVLCLPPKP KDTLVISRTP EVTCVVSGYN PYDFPIIKFK WYVDGVEVDN AKVKPRDENS         60
YNTDSVISKL TVLHQDWLNG KEYKCKVSAR EGGSSGEWYY DLWGPIECTI SKAK              114
```

```
SEQ ID NO: 13              moltype = AA   length = 114
FEATURE                    Location/Qualifiers
source                     1..114
                           mol_type = protein
                           organism = synthetic construct
SEQUENCE: 13
PSVSCLPPKP KDTFVISRTP EVTCVVSGYN PYDFPIIKFK WYVDGVEVDN AKVKPRDENS    60
YNTDSVISKL TVLHQDWLNG KEYKCKVSAR EGGSSGEWYY DLWGPIECTI SKAK         114

SEQ ID NO: 14              moltype = AA   length = 114
FEATURE                    Location/Qualifiers
source                     1..114
                           mol_type = protein
                           organism = synthetic construct
SEQUENCE: 14
PSVLCLPPKP KDTLMISRTP EVTCVVSGYN PYDFPIVKFK WYVDGVEVHN AKTKPRDENS    60
YNTDRVVSKL TVLHQDWLNG KEYKCKVSAR EGGSSGEWYY DLWGPIECTI SKAK         114

SEQ ID NO: 15              moltype = AA   length = 114
FEATURE                    Location/Qualifiers
source                     1..114
                           mol_type = protein
                           organism = synthetic construct
SEQUENCE: 15
PTVLCLPPKP KDTLMISRTP EVTCVVSGYN PYDFPIIKFK WYVDGVEVHN AKTKPRDENS    60
YNTDRVVSKL TVLHQDWLNG REYKCKVSAR EGGSSGEWYY DLWGPIECTI SKAN         114

SEQ ID NO: 16              moltype = AA   length = 114
FEATURE                    Location/Qualifiers
source                     1..114
                           mol_type = protein
                           organism = synthetic construct
SEQUENCE: 16
PSVLCLPPKP KDTLMISRTP EVTCVVSGYN PYDFPIIKFK WYVDGVEVHN GKTKPRDENS    60
YNTDRVVSKL TVLHQDWLNG KEYKCKVSAR EGGSSGEWYY DLWGPIECTI SKAK         114

SEQ ID NO: 17              moltype = AA   length = 114
FEATURE                    Location/Qualifiers
source                     1..114
                           mol_type = protein
                           organism = synthetic construct
SEQUENCE: 17
PSVLCLPPKP KDTLMISRTP EVTCVVSGYN PYDFPIIKFK WYVDGVEVHN AKTKPRDENS    60
YNTDRVVSKL TVLHQDWLNG KEYKCKVSAR EGGSSGEWYY DLWGPIECTI SKAK         114

SEQ ID NO: 18              moltype = AA   length = 114
FEATURE                    Location/Qualifiers
source                     1..114
                           mol_type = protein
                           organism = synthetic construct
SEQUENCE: 18
PSVLCLPPKP KDTLMISRTP EVTCVVSGYN PYDFPIVKFK WYVDGVEVHN AKTKPRDENS    60
YNTDRVVSKL TVLHQDWLNG KEYKCKVSAR VGGSSGEWYY DLWGPIECTI AKAK         114

SEQ ID NO: 19              moltype = AA   length = 114
FEATURE                    Location/Qualifiers
source                     1..114
                           mol_type = protein
                           organism = synthetic construct
SEQUENCE: 19
PSILCLPPKP KDTLMISRTP EVTCVVFGYN PYDFPIVKFK WYVDGVEMHN AKTKPRDENS    60
YNTDRVVSKL TVLHQDWLNG KEYKCKVSAR VGGSSGEWYY DLWGPIECTI SKAK         114

SEQ ID NO: 20              moltype = AA   length = 114
FEATURE                    Location/Qualifiers
source                     1..114
                           mol_type = protein
                           organism = synthetic construct
SEQUENCE: 20
PSVLCLPPKP NDTLMISRTP EVTCVVSGYN PYDFPIVKFK WYVDGEEVHN AKTKPREENS    60
YNTDRVVSKL TVPHQDWLNG KEYKCKVSAR VGGSSGEWYY DLWGPIECTI SKAK         114

SEQ ID NO: 21              moltype = AA   length = 114
FEATURE                    Location/Qualifiers
source                     1..114
                           mol_type = protein
                           organism = synthetic construct
SEQUENCE: 21
PSVLCLPPKP KDTLMISRTP EVTCVVSGYN PYDFPIVKFK WYVDGVEVHN AKTNPRDENS    60
```

```
YNTDRVVSKL TVLHQDWLSG KEYKCKVSAR EGGSSGEWYY NLWGPIECTI SKAK         114

SEQ ID NO: 22            moltype = AA   length = 114
FEATURE                  Location/Qualifiers
source                   1..114
                         mol_type = protein
                         organism = synthetic construct
SEQUENCE: 22
PSVLCLPPKP KDTLMISRTP EVTCVVSGYN PYDFPIVNFK WYVDGVEVHN AKTKPRDENS    60
YNTDRVVSKL TVLHQDWLNG KEYKCKVSAR EGGSSGDWYY DLWGPIECTI SKAK         114

SEQ ID NO: 23            moltype = AA   length = 114
FEATURE                  Location/Qualifiers
source                   1..114
                         mol_type = protein
                         organism = synthetic construct
SEQUENCE: 23
PSVLCLPPEP KDTLMISRTP EVTCVVSGYN PYDFPIVKFK WYVDGVEVHN AKTKPRDENS    60
YNTDRVVSKL IVLHQDWLNG KEYKCKVSAR EGGSSGEWYY DLWGPIECTI SIAK         114

SEQ ID NO: 24            moltype = AA   length = 114
FEATURE                  Location/Qualifiers
source                   1..114
                         mol_type = protein
                         organism = synthetic construct
SEQUENCE: 24
PSVLCLPPKP KDTLVISRTP EVTCVVSGYN PYDFPIIKFK WYVDGVEVDN AKVKPRDENS    60
YNTDSVVSKL TVLHQDWLNG KEYKCKVSAR VGGSSGEWYY DLWGPIECTI SKAK         114

SEQ ID NO: 25            moltype = AA   length = 114
FEATURE                  Location/Qualifiers
source                   1..114
                         mol_type = protein
                         organism = synthetic construct
SEQUENCE: 25
PSVLCLPPKP KDTLVISRTP EVTCVVSGYN PYDFPIIKFK WYVDGVEVDN AKVKPRDENS    60
YNTDSVVSKL TVLHQDWLNG KEYKCKVSAR EGGSSGEWYY DLWGPIECTI SIKS         114

SEQ ID NO: 26            moltype = AA   length = 114
FEATURE                  Location/Qualifiers
source                   1..114
                         mol_type = protein
                         organism = synthetic construct
SEQUENCE: 26
PSVHCHPPKP KDTLVISRTP EVTCVVSGYN PYDFPIIKFK WYVDGVEVDN AKVKPRDENS    60
YNTDSVVSKL TVKHQDWLNG KEYKCKVSAR EGGSSGEWYY DLWGPIECTI SKAK         114

SEQ ID NO: 27            moltype = AA   length = 114
FEATURE                  Location/Qualifiers
source                   1..114
                         mol_type = protein
                         organism = synthetic construct
SEQUENCE: 27
PSVHCHPPKP KDTLVISRTP EVTCVVSGYN PYDFPIIKFK WYVDGVEVDN AKVKPRDENS    60
YNTDSVVSKL TVKHQDWLNG KEYKCKVSAR EGGSSGEWYY DLWGPIECTI SIKS         114

SEQ ID NO: 28            moltype = AA   length = 114
FEATURE                  Location/Qualifiers
source                   1..114
                         mol_type = protein
                         organism = synthetic construct
SEQUENCE: 28
PSVLCLPPKS NDALVISRTP EVTCVVSGYN PYDFPIIKFK WYVDGVEVDN AKVKPRDENS    60
YNTDSVVSKL TILHQDWLNG KEYKCKVSAR EGGSSGEWYY DLWGPIECTI SKAK         114

SEQ ID NO: 29            moltype = AA   length = 114
FEATURE                  Location/Qualifiers
source                   1..114
                         mol_type = protein
                         organism = synthetic construct
SEQUENCE: 29
PSVLCLPPKS NDALVISRTP EVTCVVSGYN PYDFPIIKFK WYVDGVEVDN AKVKPRDENS    60
YNTDSVVSKL TILHQDWLNG KEYKCKVSAR EGGSSGEWYY DLWGPIECTI SIKS         114

SEQ ID NO: 30            moltype = AA   length = 114
FEATURE                  Location/Qualifiers
source                   1..114
                         mol_type = protein
                         organism = synthetic construct
```

```
SEQUENCE: 30
PSVHCHPPKS NDALVISRTP EVTCVVSGYN PYDFPIIKFK WYVDGVEVDN AKVKPRDENS    60
YNTDSVVSKL TIKHQDWLNG KEYKCKVSAR EGGSSGEWYY DLWGPIECTI SKAK         114

SEQ ID NO: 31           moltype = AA  length = 114
FEATURE                 Location/Qualifiers
source                  1..114
                        mol_type = protein
                        organism = synthetic construct
SEQUENCE: 31
PSVHCHPPKS NDALVISRTP EVTCVVSGYN PYDFPIIKFK WYVDGVEVDN AKVKPRDENS    60
YNTDSVVSKL TIKHQDWLNG KEYKCKVSAR EGGSSGEWYY DLWGPIECTI SIKS         114

SEQ ID NO: 32           moltype = AA  length = 114
FEATURE                 Location/Qualifiers
source                  1..114
                        mol_type = protein
                        organism = synthetic construct
SEQUENCE: 32
PSVFLFPPKP KDTLMISRTP EVTCVVVGYN PYDFPIIKFN WYVDGVEVHN AKTKPRDENS    60
YNTDSVVSVL TVLHQDWLNG KEYKCKVSAR EGGSSGEWYY DLWGPIEKTI SKAK         114

SEQ ID NO: 33           moltype = AA  length = 114
FEATURE                 Location/Qualifiers
source                  1..114
                        mol_type = protein
                        organism = synthetic construct
SEQUENCE: 33
PSVFCFPPKP KDTLMISRTP EVTCVVVGYN PYDFPIIQFN WYVDGVEVHN AKTKPRDENS    60
YNTDSVVSVL TVVHQDWLNG KEYKCKVSAR EGGSSGEWYY DLWGPIECTI SKTK         114

SEQ ID NO: 34           moltype = AA  length = 114
FEATURE                 Location/Qualifiers
source                  1..114
                        mol_type = protein
                        organism = synthetic construct
SEQUENCE: 34
PSVFCFPPKP KDTLMISRTP EVTCVVVGYN PYDFPIIQFK WYVDGVEVHN AKTKPRDENS    60
YNTDSVVSVL TVLHQDWLNG KEYKCKVSAR EGGSSGEWYY DLWGPIECTI SKTK         114

SEQ ID NO: 35           moltype = AA  length = 114
FEATURE                 Location/Qualifiers
source                  1..114
                        mol_type = protein
                        organism = synthetic construct
SEQUENCE: 35
PSVFCFPPKP KDTLMISRTP EVTCVVVGYN PYDFPIIQFN WYVDGVEVHN AKTKPRDENS    60
YNTDSVVSVL TVLHQDWLNG KEYKCKVSAR EGGSSGEWYY DLWGSIECTI SKAK         114

SEQ ID NO: 36           moltype = AA  length = 153
FEATURE                 Location/Qualifiers
source                  1..153
                        mol_type = protein
                        organism = synthetic construct
SEQUENCE: 36
PSVLCLPPKP KDTLVISRTP EVTCVVSGYN PYDFPIIKFK WYVDGVEVDN AKVKPRDENS    60
YNTDSVVSKL TVLHQDWLNG KEYKCKVSAR EGGSSGEWYY DLWGPIECTI SKAKGGSTID   120
QWLLKNAKED AIAELKKAGI TSDFYFNAIN KAK                                153

SEQ ID NO: 37           moltype = AA  length = 130
FEATURE                 Location/Qualifiers
source                  1..130
                        mol_type = protein
                        organism = synthetic construct
SEQUENCE: 37
PSVLCLPPKP KDTLVISRTP EVTCVVSGYN PYDFPIIKFK WYVDGVEVDN AKVKPRDENS    60
YNTDSVVSKL TVLHQDWLNG KEYKCKVSAR EGGSSGEWYY DLWGPIECTI SKAKQRFVTG   120
HFGGLHPANG                                                          130

SEQ ID NO: 38           moltype = AA  length = 251
FEATURE                 Location/Qualifiers
source                  1..251
                        mol_type = protein
                        organism = synthetic construct
SEQUENCE: 38
PSVLCLPPKP KDTLVISRTP EVTCVVSGYN PYDFPIIKFK WYVDGVEVDN AKVKPRDENS    60
YNTDSVVSKL TVLHQDWLNG KEYKCKVSAR EGGSSGEWYY DLWGPIECTI SKAKGGSGGS   120
GGSGGSGGSG GSGGSAVQL VESGGGLVQP GNSLRLSCAA SGFTFRSFGM SWVRQAPGKE    180
PEWVSSISGS GSDTLYADSV KGRFTISRDN AKTTLYLQMN SLKPEDTAVY YCTIGGSLSR   240
```

```
SSQGTQVTVS S                                                              251

SEQ ID NO: 39           moltype = DNA   length = 30
FEATURE                 Location/Qualifiers
source                  1..30
                        mol_type = other DNA
                        organism = synthetic construct
SEQUENCE: 39
ggttataacc cctacgactt tcctattatt                                           30

SEQ ID NO: 40           moltype = DNA   length = 27
FEATURE                 Location/Qualifiers
source                  1..27
                        mol_type = other DNA
                        organism = synthetic construct
SEQUENCE: 40
gatgagaact cttacaacac cgatagt                                              27

SEQ ID NO: 41           moltype = DNA   length = 48
FEATURE                 Location/Qualifiers
source                  1..48
                        mol_type = other DNA
                        organism = synthetic construct
SEQUENCE: 41
gcgcgagagg gtgggtcctc gggggagtgg tactacgatc tgtggggc                       48

SEQ ID NO: 42           moltype = DNA   length = 342
FEATURE                 Location/Qualifiers
source                  1..342
                        mol_type = other DNA
                        organism = synthetic construct
SEQUENCE: 42
ccgtcagtct tgtgcctgcc cccaaaaccc aaggacaccc tcgtgatctc ccggacccct          60
gaggtcacat gcgtggtgtc tggttataac ccctacgact ttcctattat taagttcaaa         120
tggtacgtgg acggcgtgga ggtggataat gccaaggtaa agccgcggga tgagaactct         180
tacaacaccg atagtgtggt cagcaaactc accgtcctgc accaggactg gctgaatggc         240
aaggagtaca agtgcaaggt cagtgcgcga gagggtgggt cctcggggga gtggtactac         300
gatctgtggg gccccatcga atgcaccatc tccaaagcca aa                            342
```

C-BASED SINGLE DOMAIN ANTIBODY FOR NEUTRALIZING RESPIRATORY SYNCYTIAL VIRUS AND APPLICATION THEREOF

CROSS-REFERENCE OF RELATED APPLICATIONS

The present application is a continuation-application of International Patent Application (PCT) No. PCT/CN2023/115623 filed on Aug. 29, 2023, which claims foreign priorities of Chinese Patent Application No. 202211049964.6, filed on Aug. 30, 2022, the entire contents of which are hereby incorporated by reference.

SEQUENCE LISTING

The instant application contains a Sequence Listing which has been submitted electronically in ASCII format and is hereby incorporated by reference in its entirety. Said ASCII copy, created on Jul. 11, 2024, is named Sequence Listing.xml and is 41,383 bytes in size.

TECHNICAL FIELD

The present invention relates to the technical field of bio-pharmaceuticals, specifically to a C-based single domain antibody that neutralizes respiratory syncytial virus (RSV) and application thereof.

BACKGROUND

Respiratory syncytial virus is seasonal and can be transmitted through the respiratory tract and close contact. It mainly infects infants, young children, the elderly, and people with low immunity, causing acute respiratory infection, pneumonia, and even death. So far, there have been no effective vaccines and specific therapeutic drugs for treating respiratory syncytial virus. In the clinical practice, Ribavirin (non-specific, high side effects) or preventive injection of Palivizumab monoclonal antibody (expensive, weak neutralizing activity) are used to achieve antiviral effect. Considering this, there is an urgent need to develop a new generation of drugs for dealing with respiratory syncytial virus.

SUMMARY OF THE INVENTION

In view of the problems in the prior art, the present invention provides a C-based single domain antibody that neutralizes respiratory syncytial virus and application thereof.

In the present invention, using a phage surface display library with the transformed CH2-m01sm2 of the CH2 domain of the human IgG1 as the skeleton and the respiratory syncytial virus envelope protein F (RSV F protein) as an antigen, the candidate clone is obtained by screening against the RSV F protein and the subsequent transformation. We use *Escherichia coli* prokaryotic expression and purify the cloned protein, and identify the biological specificity, neutralization activity thereof, and finally obtain a C-based single-domain antibody BBT-VC001-1 (also referred to as C-type nanobody BBT-VC001-1) capable of neutralizing respiratory syncytial virus, which can be used for the prevention and treatment of respiratory syncytial virus.

BBT-VC001-1 has three loop regions. The amino acid sequences of the three loop regions, Loop 1, Loop 2, and Loop 3 are set forth in SEQ ID No: 1, SEQ ID No: 3 and SEQ ID No: 6 respectively.

The nucleotide sequences encoding the three loop regions Loop 1, Loop 2 and Loop 3 in BBT-VC001-1 are set forth in SEQ ID No: 39, SEQ ID No: 40 and SEQ ID No: 41 respectively.

The amino acid sequence of BBT-VC001-1 is set forth in SEQ ID No: 10, and the nucleotide sequence is set forth in SEQ ID No: 42.

The C-based single domain antibody BBT-VC001-1 for RSV F protein provided by the present invention is obtained by the following method: firstly, constructing a phage display library using CH2 (FIG. 1) as a skeleton, then using the RSV F protein as an antigen, and screening and optimizing to obtain a cloned BBT-VC001-1. Expression and purifying the clone, and identifying and analyzing the clone (FIG. 2). The binding ability of BBT-VC001-1 is identified by ELISA, and experimental results show that BBT-VC001-1 can be specifically combined with RSV F protein (FIG. 3). Indirect immunofluorescence experiments show that BBT-VC001-1 can also be combined with the F protein with a natural conformation on the surface of the cell membrane (FIG. 4). In addition, cell level antiviral experiments show that BBT-VC001-1 has an efficient anti-respiratory syncytial virus effect (FIG. 5A-5B). Animal level experiments show that Balb/c mice infected with RSV can be prevented and treated by pulmonary atomization of the BBT-VC001-1 antibody (FIG. 6A-6C).

The amino acid sequence point mutants of the BBT-VC001-1 antibody of the present invention are named 2C, M17, ZH1, B5, M2, M3, M4, M5, M6, M7, M8, M9, M10, M11, KS, 2H, 2H-KS, F11, F11-KS, 2H-F11, 2H-F11-KS; and these mutant antibodies have a binding activity and antiviral activity similar to that of the BBT-VC001-1 antibody (FIG. 7-10). Meanwhile, after the corresponding parts of other antibody fragments are replaced with three loop regions of BBT-VC001-1 (the resulting antibodies are hIgG1 CH2-com, hIgG2 CH2-com, hIgG3 CH2-com, hIgG4 CH2-com), their binding ability and antiviral activity can still remain (FIG. 11A-11B). Furthermore, when BBT-VC001-1 is linked to a polypeptide (ABD and 16 L) or protein (VH) to form a fusion polypeptide or fusion protein, the antigen-binding activity remains unchanged (FIG. 12). The sequence numbers of all the above mutants and antibodies are listed in Table 1.

The present disclosure also provides the application of the above-mentioned C-based single domain antibody that neutralizes respiratory syncytial virus in the preparation of preventive and therapeutic drugs, detection probes, fusion polypeptides, fusion proteins, and coupled antibodies against respiratory syncytial virus. The C-based single domain antibody that neutralizes respiratory syncytial virus of the present invention can be used in the preparation of nasal drops, nasal sprays, aerosols, intramuscular injection preparations, and intravenous injection preparations related to the prevention and treatment of respiratory syncytial virus, preferably, the concentration range in each formula is from 0.01 ng/ml to 1 g/mL.

The term "C-based single domain antibody" used in the present invention refers to a type of antibody with the antibody constant domain CH2 as the backbone. Compared with full-length monoclonal antibodies, single domain antibodies have better tissue penetration and can advantageously bind to epitopes with steric hindrance.

The beneficial effects of the present invention are as follows: the C-based single domain antibody of the present invention is an antibody against RSV F protein, can inhibit the virus from invading cells, can be used for the prevention, treatment and diagnosis of RSV, and can be used to further study the mechanism of RSV infection. Compared with full-length monoclonal antibodies (molecular weight ~150 kDa), the C-based single domain antibody of the present invention has a smaller molecular weight (12~15 kDa), has better tissue permeability and the ability to bind to antigenic epitopes with steric hindrance effects; it can be expressed in multiple expression systems, including prokaryotic, yeast, and mammalian cells, with a low production cost and a short production cycle. C-based single domain antibodies have a wide range of administration routes and can be administered through nasal drops, nasal sprays, aerosol inhalation, intramuscular injection, subcutaneous injection, intravenous injection, etc.

DRAWINGS

FIG. 7 shows binding ability of the mutants obtained by point mutations in the loop regions and/or backbones of BBT-VC001-1, whose $EC_{50}$ values comparable to BBC-VC001-1.

FIG. 8 shows antiviral activity of 2C, M17, Zh1, B5, M2, M3, M14 in the mutants of BBT-VC001-1 shown in FIG. 7, whose $IC_{50}$ values comparable to BBC-VC001-1.

FIG. 9 shows antiviral activity of M5-M11 in the mutants of BBT-VC001-1 shown in FIG. 7, whose $IC_{50}$ values comparable to BBC-VC001-1.

FIG. 10 shows antiviral activity of KS, 2H, 2H-KS, F11, F11-KS, 2H-F11, 2H-F11-KS in the mutants of BBT-VC001-1 shown in FIG. 7, whose $IC_{50}$ values comparable to BBC-VC001-1.

FIG. 11A shows the binding ability of the resulting combinators obtained by replacing the sequences of three loop regions in BBT-VC001-1 into the loop regions in CH2 backbones of different antibodies.

FIG. 11B shows the antiviral activity of the resulting combinators obtained by replacing the sequences of three loop regions in BBT-VC001-1 into the loop regions in CH2 backbones of different antibodies.

FIG. 12 shows binding ability of BBT-VC001-1 coupled with peptides or proteins.

DETAILED DESCRIPTION

Figure 1:
FIG. 1 shows a schematic diagram of the structure of the C-based single domain antibody. The C-domain antibody has a backbone derived from CH2 domain of the constant domain of IgG1, and includes three flexible loop regions (Loop1, Loop2, and Loop3) corresponding to the three complementarity-determining regions (CDRs) in the variable regions of the antibody.

The present invention is described in detail in combination with the embodiments and attached drawings. The following embodiments are implemented on the premise of the technical scheme of the invention of the present invention, and the detailed implementations and specific operation processes are given. However, the scope of protection of the present invention is not limited to the following embodiments.

Definition

CH2: The isolated human IgG1 constant domain 2. The CH2 domain of the human IgG1 used as the skeleton is from Chain A, Ig gamma-1 chain C region (PDB: 3DJ9_A, National Library of Medicine, National Center for Biotechnology Information (NCBI)). The sequence we used is the position 3-105 of protein 3DJ9_A. CH2-m01sm2 was genetically engineered from CH2 sequence above.

C-based single-domain antibody: an antibody based on scaffold derived from immunoglobulin constant CH2 domain.

Embodiment 1: Expression and Purification of Human Respiratory Syncytial Virus Envelope Protein recF According to the gene sequence of RSV (GenBank No. M11486.1), the gene encoding RSV envelope protein F was fused with the gene encoding the Fc fragment of antibody IgG1, to prepare the gene encoding recombinant F protein (recF). The gene was then ligated to the vector pSecTag2A, transformed, and cloned to construct the eukaryotic expression plasmid pSecTag2A-recF. One day before transfection, 40 mL of 293F cells (with the cell density of $5\text{-}10\times10^5$ cells/mL) were inoculated into 125 mL suspension culture vessels. 40 μg of plasmids (pSecTag2A-recF) were diluted in 4 mL of culture medium and gently mixed, and 120 μL of PEI (polyethylenimine) was diluted in the same culture medium and gently mixed. The culture medium was added drop by drop to the cells after incubation for 20 min at room temperature. The cells were placed in a suspension incubator at 250 rpm/min and 37° C. The supernatant of the medium was collected after 144 h. Protein expression was detected by protein immunoblotting (Western Blot) with HRP-anti-human Fc.

After detection of target protein expression, cell culture and transfection were scaled up to express the protein recF in large quantities. Medium supernatants were collected, and the target protein was purified with Protein A resins. Then ultrafiltered and replaced the buffer using ultrafiltration centrifuge tubes with a molecular weight cut-off of 10 kDa. After concentration, verify the purity of the target protein by SDS-PAGE.

Embodiment 2: Construction and Screening of Phage Display Library

A phage display library with human CH2 backbone was constructed according to existing literature (Gong R., et al., PLOS One, 2012, 7: e42288), and screened with eukaryotic-expressed antigen recF. After the purified antigen was combined to magnetic beads, screened candidate antibodies with the phage display library. The recF-specific phages could be captured by the antigen, yielding candidate clones. By further affinity maturation of the candidate clones (Wang R., et al., Virol Sin., 2021, 11:1-11), C-based single domain antibody BBT-VC001-1 was obtained.

BBT-VC001-1 was sequenced and the three loop regions were Loop1, Loop2 and Loop3, whose gene sequences and amino acid sequences are listed in Table 1 respectively.

Embodiment 3: The Expression and Purification of BBT-VC-001

Figure 2:
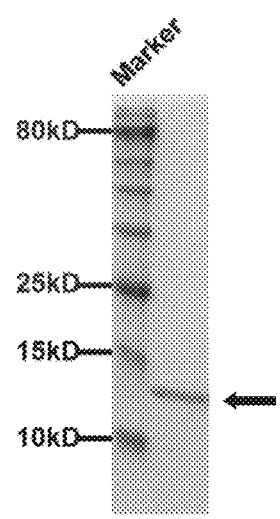
FIG. 2 shows the expression and purification of BBT-VC001-1. The proteins are detected by polyacrylamide gel electrophoresis (SDS-PAGE), and the lanes from left to right are protein molecular weight standards (Marker) and purified BBT-VC001-1.

BBT-VC001-1 was expressed and purified according to the existing literature (Gong R., et al., Methods Mol Biol., 2012, 899:85-102). The BBT-VC001-1 in prokaryotic expression vector was transformed into *E. coli* HB2151. The monoclonal colonies were picked and inoculated in SB medium with 100 μg/mL ampicillin (1 L medium contains 30 g tryptone, 20 g yeast extract and 10 g MOPS, and the pH of the medium was adjusted to 7.0 with NaOH). When the OD600 of the above SB medium reached 0.7-1.0, IPTG was added to a final concentration of 200 μg/ml, and induced expression was carried out at 37° C., 220 rpm for 14-16 h. The organisms were collected by centrifugation at 4° C., 6000 rpm, 15 min. Discarded the medium, and resuspended the precipitate in PBS (pH 7.0). After treatment with polymyxin B for 1 h, collected the supernatant by centrifugation. The supernatant was then purified with Ni-NTA Agarose and verified by SDS-PAGE, shown in FIG. 2. Above supernatant was subsequently concentrated by ultrafiltration using an ultrafiltration centrifuge tube with a molecular weight cut-off of 3 kDa. The C-terminus of the obtained BBT-VC001-1 contained a 6× His tag and a FLAG tag.

Figure 3:
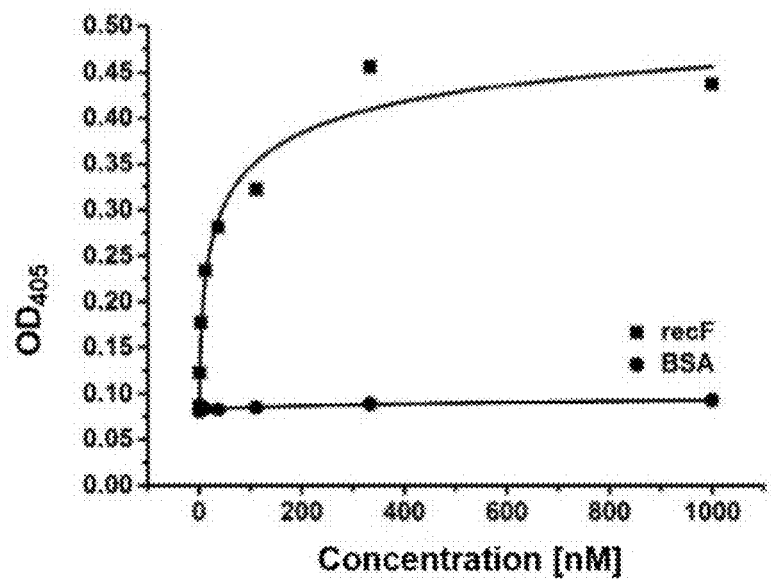
FIG. 3 shows the binding of BBT-VC001-1 to the human respiratory syncytial virus envelope protein F determined by ELISA. The $EC_{50}$ of the binding ability of BBT-VC001-1 to F protein is 28 nM, with bovine serum albumin (BSA) as a negative control.

Embodiment 4: Determination of the Binding of BBT-VC001-1 to the Recombinant Envelope Protein recF with ELISA recF (4 μg/mL) was coated on an ELISA plate and incubated overnight at 4° C. and then blocked with PBS+3% milk at 37° C. for 1 h. BBT-VC001-1 with a gradient dilution was added and incubated at 37° C. for 2 h. The plate was then washed four times with PBST (PBS+0.05% Tween 20) and then incubated with HRP-Anti-FLAG monoclonal antibody at 37° C. for 1 h. The ABTS was added for color development. Bovine serum albumin (BSA) was used as a negative control. The $EC_{50}$ of BBT-VC001-1 binding to recF is 28 nM, and BBT-VC001-1 does not bind to BSA. The results are shown in FIG. 3.

Figure 4:
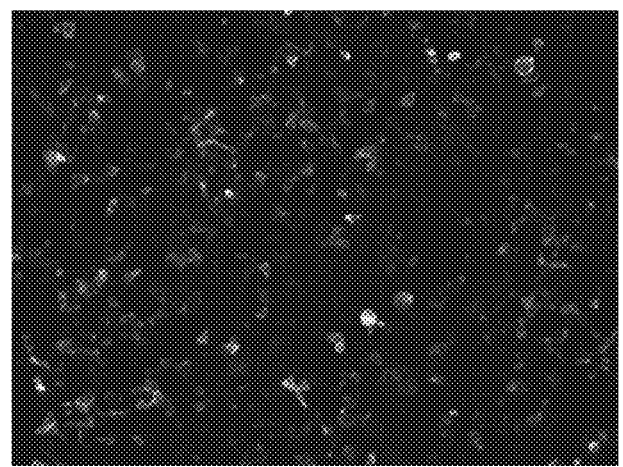
FIG. 4 shows indirect immunofluorescence determination of the binding of BBT-VC001-1 to the natural F protein on the surface of human respiratory syncytial virus particles. BBT-VC001-1 binding to F protein on the surface of human respiratory syncytial virus particles show fluorescence after staining with fluorescent secondary antibody.

Embodiment 5: Indirect Immunofluorescence Determination of the Binding of BBT-VC001-1 to the Natural F Protein on the Surface of Human Respiratory Syncytial Virus Particles 100 μL of Hep-2 ($2\times10^5$ cells/mL) cells were inoculated into 96-well plates and cultured for 14-16 h. Washed the cells with PBS, and respiratory syncytial virus (100 PFU/well) was added to infect the cells for 1 h. Then discarded the virus and continued to culture at 37° C. by replenishing with 100 μL of DMEM containing 2% fetal bovine serum. After about 48 h, the cells were fixed in 4% formaldehyde solution for 30 min and blocked with 5% BSA for 1 h. The cells were sequentially incubated with BBT-VC001-1 as primary antibody and FITC-Anti-His as secondary antibody. Observed the staining results with fluorescence microscopy (FIG. 4).

Figure 5:
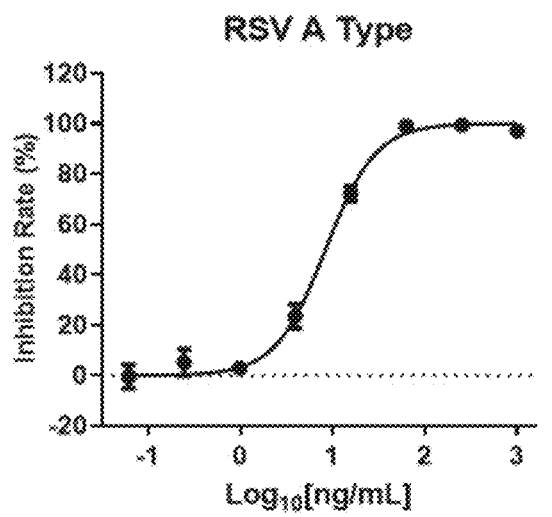
FIG. 5A shows that in the neutralization assay of BBT-VC001-1 to human respiratory syncytial virus; the $IC_{50}$ for the inhibition of respiratory syncytial virus type A (RSV A) by BBT-VC001-1 is 8.326 ng/mL.
FIG. 5B shows that in the neutralization assay of BBT-VC001-1 to human respiratory syncytial virus; the $IC_{50}$ for the inhibition of respiratory syncytial virus B (RSV B) is 8.419 ng/ml.
Figure 5:
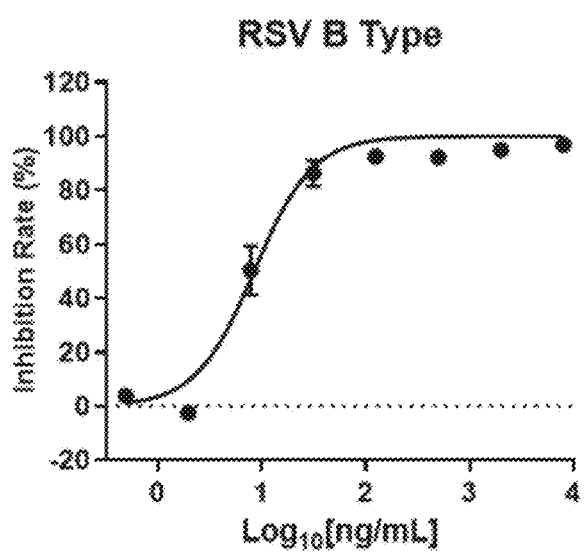

Embodiment 6: Inhibition of Human Respiratory Syncytial Virus Replication by BBT-VC001-1 Antibody in Hep-2 Cells 100 μL of Hep-2 ($2\times10^5$ cells/mL) cells were inoculated in 96-well plates and cultured for 14-16 h. Respiratory syncytial viruses (types A or B) were mixed and incubated with different concentrations of BBT-VC001-1 antibody for 1 h, then the mixture was added to the PBS-washed cells, and the cells continued to be cultured at 37° C. After 24 h-48 h, the cells were fixed in 4% formaldehyde solution for 30 min and blocked with 5% BSA for 1 h. The cells were sequentially incubated with IgG-mpe8 as primary antibody and FITC-Anti-human as secondary antibody, then photographed and analyzed by using a high content cell analyzer. The inhibition rate of viral infection in each well was calculated according to the test results with reference to the negative and positive control wells. The $IC_{50}$ of BBT-VC001-1 for inhibition of respiratory syncytial virus type A was 8.326 ng/ml (FIG. 5A); and the $IC_{50}$ for inhibition of type B was 8.419 ng/ml (FIG. 5B).

Figure 6:
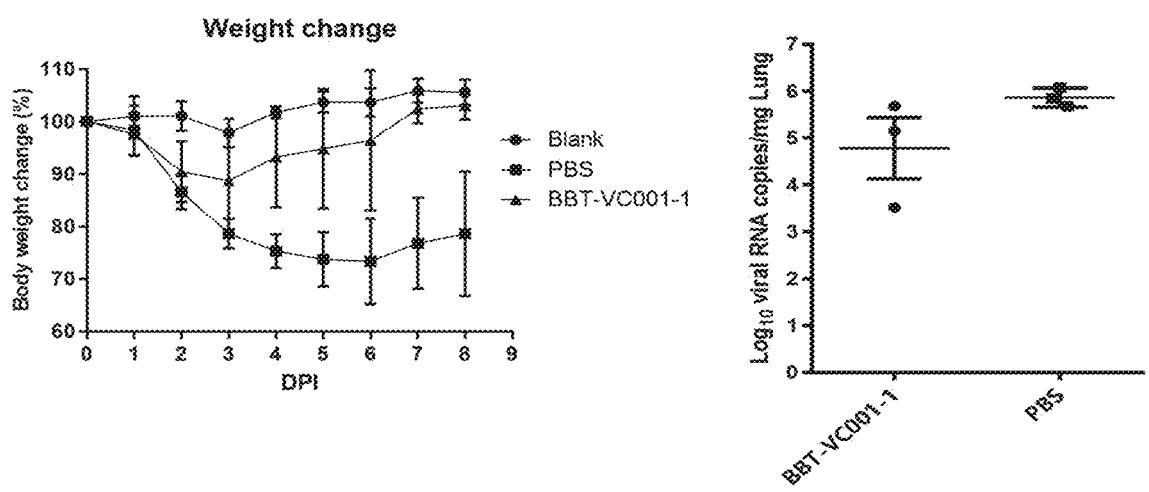
FIG. 6A shows prophylactic effects of BBT-VC001-1 on human respiratory syncytial virus infection in Balb/c mice. Prophylactic administration of BBT-VC001-1 by lung nebulization protects mice against weight loss.
FIG. 6B shows prophylactic effects of BBT-VC001-1 on human respiratory syncytial virus infection in Balb/c mice. Prophylactic administration of BBT-VC001-1 by lung nebulization reduces lung viral load (viral RNA copies).
FIG. 6C shows therapeutic effects of BBT-VC001-1 on human respiratory syncytial virus infection in Balb/c mice. Therapeutic administration of BBT-VC001-1 by lung nebulization significantly reduces viral load (viral titer) in the lungs.
Figure 6:
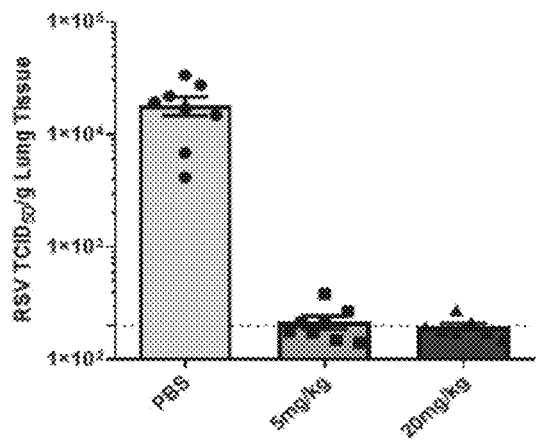

Embodiment 7: Protective Effect of BBT-VC001-1 Against RSV Infection in a Mouse Model Prophylactic antiviral: Before viral infection, Balb/c mice were anesthetized and administered with antibodies at a dose of 2.5 mg/kg (prophylactic group) or 50 μL PBS (blank and PBS group) by lung nebulization. Six hours later, RSV A2 virus was administered to every mouse by nasal drip at the dose of $1\times10^7$ FFU in the prophylactic and PBS groups. After that, weighted the mice every day. Anaesthetized and executed some mice on the fourth day after infection and took lung tissues to determine the viral load. The results are shown in FIG. 6A. Compared with the PBS group, the prophylactic group showed a significant regain in body weight and a lower viral load in lung tissue.

Therapeutic antiviral: First, the mice were anaesthetized and infected with $1\times10^7$ FFU of RSV A2 per mouse by nasal drip. Three hours later, administered different doses (5 mg/kg and 20 mg/kg) of BBT-VC001-1 by lung nebulization in a volume of 50 μL per mouse in therapeutic group, and 50 μL of PBS to the lungs in control group. Administer the antibodies once the first and the second day. The mice were anaesthetized and executed on the fourth day after the infection, and lung tissue was taken to determine the viral titer. The results are shown in FIG. 6C, which shows that the viral titers of lung tissues of mice in the antibody administration group were significantly reduced.

Embodiment 8: The Construction and Activity of the Point Mutants, Combinators, and Fusion Proteins of BBT-VC001-1

Construction and activity of the point mutants. By single or multiple mutations in the loop regions and/or the backbones of BBT-VC001-1, different sequences were obtained (2C(L4S, L14F), M17 (V67I), Zh1 (L4S, L14F, V67I), B5 (V15M, I37V, D49H, V53T, S65R), M2 (S2T, V15M, D49H, V53T, S65R, K81R, K114N), M3 (V15M, D49H, A51G, V53T, S65R), M4 (V15M, D49H, V53T, S65R), M5 (V15M, I37V, D49H, V53T, S65R, E91V, S111A), M6 (V3I, V15M, S27F, I37V, V48M, D49H, V53T, S65R, E91V), M7 (K11N, V15M, I37V, V46E, D49H, V53T, D57E, S65R, L73P, E91V), M8 (V15M, I37V, D49H, V53T, K54N, S65R, N79S, D101N), M9 (V15M, I37V, K38N, D49H, V53T, S65R, E97D), M10 (K9E, V15M, I37V, D49H, V53T, S65R, T71I, K112I), M11 (E91V), KS(K112I, A113K, K114S), 2H (L4H, L6H, L73K), 2H-KS (L4H, L6H, L73K, K112I, A113K, K114S), F11 (P10S, K11N, T13A, V72I), F11-KS (P10S, K11N, T13A, V72I, K112I, A113K, K114S), 2H-F11 (L4H, L6H, P10S, K11N, T13A, V72I, L73K), 2H-F11-KS (L4H, L6H, P10S, K11N, T13A, V72I, L73K, K112I, A113K, K114S). Mutants were synthesized by gene synthesis company and constructed into expression vectors for protein expression as described in embodiment 3. The mutant proteins were subjected by ELISA and antiviral assays as described in embodiment 4 and embodiment 6. The binding ability of above point mutant proteins to the recombinant envelope protein recF of RSV is 20-150 nM, and the antiviral activity against the RSV A2 strain is 3-55 ng/ml. The results indicate that mutants obtained by some point mutations in the loop and/or backbone regions of BBT-VC001-1 protein remain active.

The construction and activity of combinations: Sequences of three loop regions from BBT-VC001-1 (loop 1, loop 2, and loop 3) were replaced into the loop regions in CH2 backbones of different types of antibodies: Human IgG1 CH2 region, IgG2 CH2 region, IgG3 CH2 region, IgG4 CH2 region. The combinations obtained were named as hIgG1 CH2-com, hIgG2 CH2-com, hIgG3 CH2-com, hIgG4 CH2-com respectively. Then, gene synthesis, protein expression, and activity assay were carried out. (same methods mentioned above). The results shown in FIG. 11A-11B indicate that hIgG1 CH2-com, hIgG2 CH2-com, hIgG3 CH2-com, hIgG4 CH2-com have comparable binding ability and antiviral activity in cellular level. The results indicate that 3 loop regions of BBT-VC001-1 can work in different backbones.

The construction and activity of fusions: BBT-VC001-1 was linked with peptides (16 L and ABD), or proteins (VH) and named BBT-VC001-1-16 L, BBT-VC001-1-ABD, BBT-VC001-1-VH, respectively. Then, gene synthesis, protein expression, and activity assay were carried out (same methods mentioned above). The results shown in FIG. 12 indicate that BBT-VC001-1 still maintains binding activity after fusion of peptides or proteins. BBT-VC001-1 can be used to prepare fusion polypeptides and fusion proteins for the prevention and treatment of human respiratory syncytial virus.

Finally, a table of sequence information of all antibodies and fragments thereof involved in the above embodiments is attached.

TABLE 1

Sequence information of antibodies and their loops

| Seq ID | description | Seq Type | Note |
| --- | --- | --- | --- |
| SEQ ID No: 1 | BBT-VC001-1 Loop1 | Amino acid | |
| SEQ ID No: 2 | M5 Loop1 | Amino acid | |
| SEQ ID No: 3 | BBT-VC001-1 Loop2 | Amino acid | |
| SEQ ID No: 4 | B5 Loop2 | Amino acid | |
| SEQ ID No: 5 | M7 Loop2 | Amino acid | |
| SEQ ID No: 6 | BBT-VC001-1 Loop3 | Amino acid | |
| SEQ ID No: 7 | M5 Loop3 | Amino acid | |
| SEQ ID No: 8 | M8 Loop3 | Amino acid | |
| SEQ ID No: 9 | M9 Loop3 | Amino acid | |
| SEQ ID No: 10 | BBT-VC001-1 | Amino acid | |
| SEQ ID No: 11 | 2C | Amino acid | mutation sites: L4S, L14F |
| SEQ ID No: 12 | M17 | Amino acid | mutation site: V67I |
| SEQ ID No: 13 | Zh1 | Amino acid | mutation sites: L4S, L14F, V67I |
| SEQ ID No: 14 | B5 | Amino acid | mutation sites: V15M, I37V, D49H, V53T, S65R |
| SEQ ID No: 15 | M2 | Amino acid | mutation sites: S2T, V15M, D49H, V53T, S65R, K81R, K114N |
| SEQ ID No: 16 | M3 | Amino acid | mutation sites: V15M, D49H, A51G, V53T, S65R |
| SEQ ID No: 17 | M4 | Amino acid | mutation sites: V15M, D49H, V53T, S65R |
| SEQ ID No: 18 | M5 | Amino acid | mutation sites: V15M, I37V, D49H, V53T, S65R, E91V, S111A |
| SEQ ID No: 19 | M6 | Amino acid | mutation sites: V3I, V15M, S27F, I37V, V48M, D49H, V53T, S65R, E91V |
| SEQ ID No: 20 | M7 | Amino acid | mutation sites: K11N, V15M, I37V, V46E, D49H, V53T, D57E, S65R, L73P, E91V |

TABLE 1-continued

Sequence information of antibodies and their loops

| Seq ID | description | Seq Type | Note |
|---|---|---|---|
| SEQ ID No: 21 | M8 | Amino acid | mutation sites: V15M, I37V, D49H, V53T, K54N, S65R, N79S, D101N |
| SEQ ID No: 22 | M9 | Amino acid | mutation sites: V15M, I37V, K38N, D49H, V53T, S65R, E97D |
| SEQ ID No: 23 | M10 | Amino acid | mutation sites: K9E, V15M, I37V, D49H, V53T, S65R, T71I, K112I |
| SEQ ID No: 24 | M11 | Amino acid | mutation site: E91V |
| SEQ ID No: 25 | KS | Amino acid | mutation sites: K112I, A113K, K114S |
| SEQ ID No: 26 | 2H | Amino acid | mutation sites: L4H, L6H, L73K |
| SEQ ID No: 27 | 2H-KS | Amino acid | mutation sites: L4H, L6H, L73K, K112I, A113K, K114S |
| SEQ ID No: 28 | F11 | Amino acid | mutation sites: P10S, K11N, T13A, V72I |
| SEQ ID No: 29 | F11-KS | Amino acid | mutation sites: P10S, K11N, T13A, V72I, K112I, A113K, K114S |
| SEQ ID No: 30 | 2H-F11 | Amino acid | mutation sites: L4H, L6H, P10S, K11N, T13A, V72I, L73K |
| SEQ ID No: 31 | 2H-F11-KS | Amino acid | mutation sites: L4H, L6H, P10S, K11N, T13A, V72I, L73K, K112I, A113K, K114S |
| SEQ ID No: 32 | hIgG1 CH2-com | Amino acid | three loop regions from BBT-VC001-1 are replaced into different antibody backbones |
| SEQ ID No: 33 | hIgG2 CH2-com | Amino acid | |
| SEQ ID No: 34 | hIgG3 CH2-com | Amino acid | |
| SEQ ID No: 35 | hIgG4 CH2-com | Amino acid | |
| SEQ ID No: 36 | BBT-VC001-1-ABD | Amino acid | BBT-VC001-1 linked with peptide or protein |
| SEQ ID No: 37 | BBT-VC001-1-16L | Amino acid | |
| SEQ ID No: 38 | BBT-VC001-1-VH | Amino acid | |
| SEQ ID No: 39 | BBT-VC001-1 Loop1 | Nucleotide | |
| SEQ ID No: 40 | BBT-VC001-1 Loop2 | Nucleotide | |
| SEQ ID No: 41 | BBT-VC001-1 Loop3 | Nucleotide | |
| SEQ ID No: 42 | BBT-VC001-1 | Nucleotide | |

With the help of the embodiments, those skilled in the art can understand and master the present invention better. However, the scope of protection and claims thereof is not limited to the provided embodiments. Based on the embodiments in the present invention, all other embodiments obtained by those skilled in the art without creative work are within the scope of protection of the present invention.

What is claimed is:

1. An antibody for neutralizing respiratory syncytial virus, wherein the antibody employs a CH2 domain as a backbone and is termed a C-based single domain antibody; wherein the C-based single domain antibody comprises three loop regions: Loop 1, Loop 2, and Loop 3;

and wherein the amino acid sequence of Loop 1 comprises one of SEQ ID No: 1 to SEQ ID No: 2;

the amino acid sequence of Loop 2 comprises one of SEQ ID No: 3 to SEQ ID No: 5;

and the amino acid sequence of Loop 3 comprises one of SEQ ID No: 6 to SEQ ID No: 9.

2. The antibody of claim 1, wherein the amino acid sequences of Loop 1, Loop 2, and Loop 3, respectively, comprise SEQ ID No: 1, SEQ ID No: 3, and SEQ ID No: 6.

3. The antibody of claim 1, wherein the amino acid sequence of the C-based single domain antibody comprises one of SEQ ID No: 10 to SEQ ID No: 35.

4. The antibody of claim 2, wherein the encoding DNA sequences of Loop 1, Loop 2, and Loop 3, respectively, comprise SEQ ID No: 39, SEQ ID No: 40, and SEQ ID No: 41.

5. The antibody of claim 3, wherein the encoding DNA sequence of the C-based single domain antibody comprises SEQ ID No: 42.

6. A respiratory syncytial virus antibody fusion polypeptide, comprising SEQ ID No: 36.

7. A respiratory syncytial virus antibody fusion polypeptide, comprising SEQ ID No: 37.

8. A respiratory syncytial virus antibody fusion protein, comprising SEQ ID No: 38.

* * * * *